US011760786B2

(12) United States Patent
Bonifant et al.

(10) Patent No.: US 11,760,786 B2
(45) Date of Patent: Sep. 19, 2023

(54) CHIMERIC ANTIGEN RECEPTORS TARGETING ABNORMAL GLYCOBIOLOGY

(71) Applicant: The Regents of The University Of Michigan, Ann Arbor, MI (US)

(72) Inventors: Challice L. Bonifant, Towson, MD (US); Alnawaz Rehemtulla, Plymouth, MI (US); David M. Markovitz, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 550 days.

(21) Appl. No.: 16/782,417

(22) Filed: Feb. 5, 2020

(65) Prior Publication Data

US 2020/0247868 A1 Aug. 6, 2020

Related U.S. Application Data

(60) Provisional application No. 62/802,001, filed on Feb. 6, 2019.

(51) Int. Cl.
| | |
|---|---|
| *C07K 14/725* | (2006.01) |
| *C07K 14/705* | (2006.01) |
| *A61K 35/17* | (2015.01) |
| *A61P 35/00* | (2006.01) |
| *C12N 5/0783* | (2010.01) |

(52) U.S. Cl.
CPC .......... *C07K 14/7051* (2013.01); *A61K 35/17* (2013.01); *A61P 35/00* (2018.01); *C07K 14/70517* (2013.01); *C07K 14/70575* (2013.01); *C12N 5/0636* (2013.01); *C07K 2319/02* (2013.01)

(58) Field of Classification Search
None
See application file for complete search history.

(56) References Cited

U.S. PATENT DOCUMENTS

| | | | | |
|---|---|---|---|---|
| 4,946,778 | A | 8/1990 | Ladner et al. | |
| 5,260,203 | A | 11/1993 | Ladner et al. | |
| 2014/0271635 | A1 | 9/2014 | Brogdon et al. | |
| 2015/0080293 | A1 | 3/2015 | Markovitz et al. | |
| 2017/0267739 | A1* | 9/2017 | Berger | C07K 14/7051 |
| 2017/0291928 | A1* | 10/2017 | Markovitz | A61K 38/168 |
| 2018/0049412 | A1 | 2/2018 | Shen | |
| 2018/0169260 | A1* | 6/2018 | Demetriou | A61K 38/168 |
| 2018/0371057 | A1 | 12/2018 | Skinner | |

FOREIGN PATENT DOCUMENTS

WO WO 88/01649 3/1988

OTHER PUBLICATIONS

Jena et al. (Blood Aug. 19, 2010 116(7): 1035-1044) (Year: 2010).*
Swanson et al. (Cell Oct. 22, 2015, 163: 746-758) (Year: 2015).*
Hooper et al. (Structure May 2, 2017 25:773-782) (Year: 2017).*
International Search Report and Written Opinion for PCT/US20/16749, dated May 27, 2020. 20 pages.
Extended European Search Report for PCT/US2020016749, dated Aug. 24, 2022. 10 pages.
Andre'et al., Lectins: getting familiar with translators of the sugar code. Molecules. Jan. 22, 2015;20(2):1788-823.
Ausubel et al., Current Protocols in Molecular Biology, Greene Publishing Associates and John Wiley & Sons, NY, 1994. TOC only. 14 pages.
Barber et al., Treatment of multiple myeloma with adoptively transferred chimeric NKG2D receptor-expressing T cells. Gene Ther. May 2011;18(5):509-16.
Borrebaeck et al., Lectins as Mitogens. Adv. Lectin Res., 1989; 2: 1-27.
Brash et al., Strontium phosphate transfection of human cells in primary culture: stable expression of the simian virus 40 large-T-antigen gene in primary human bronchial epithelial cells. Mol Cell Biol. May 1987;7(5):2031-4.
Chothia et al., Canonical structures for the hypervariable regions of immunoglobulins. J Mol Biol. Aug. 20, 1987;196(4):901-17.
Chothia et al., Conformations of immunoglobulin hypervariable regions. Nature. Dec. 21-28, 1989;342(6252):877-83.
Christodoulou et al., 63rd ASH Annual Meeting Abstracts: Poster Abstracts 703. Cellular Immunotherapies: Basic and Translational. CAR-NK Cells Targeting Sars-Cov-2 Glycosites As COVID-19 Treatment. Blood. 2021: 138; 2803-2804.
Christodoulou et al., Glycoprotein Targeted CAR-NK Cells for the Treatment of SARS-CoV-2 Infection. Front Immunol. Dec. 23, 2021;12:763460. 10 pages.
Coves-Datson et al., Inhibition of Ebola Virus by a Molecularly Engineered Banana Lectin. PLoS Negl Trop Dis. Jul. 29, 2019;13(7):e0007595. 1-20.
Gabius et al., From lectin structure to functional glycomics: principles of the sugar code. Trends Biochem Sci. Jun. 2011;36(6):298-313.
Gabius et al., The glycobiology of the CD system: a dictionary for translating marker designations into glycan/lectin structure and function. Trends Biochem Sci. Jul. 2015;40(7):360-76.
Gattinoni et al., Adoptive immunotherapy for cancer: building on success. Nat Rev Immunol. May 2006;6(5):383-93.
Ghanem et al., Bispecific chimeric antigen receptors targeting the CD4 binding site and high-mannose Glycans of gp120 optimized for anti-human immunodeficiency virus potency and breadth with minimal immunogenicity. Cytotherapy. Mar. 2018;20(3):407-419.
Hopper et al., The Tetrameric Plant Lectin BanLec Neutralizes HIV through Bidentate Binding to Specific Viral Glycans. Structure. May 2, 2017;25(5):773-782.e5.

(Continued)

*Primary Examiner* — Peter J Reddig

(74) *Attorney, Agent, or Firm* — CASIMIR JONES, SC; David W. Staple

(57) ABSTRACT

The disclosure provides a chimeric antigen receptor (CAR) polypeptide having an antigen binding domain comprising an extracellular lectin which specifically binds to glycoproteins expressed on the surface of target cells. Also provided herein are engineered lymphocytes expressing the CAR polypeptide, a nucleic acid molecule encoding the CAR polypeptide, and methods of treating cancer.

13 Claims, 9 Drawing Sheets

Specification includes a Sequence Listing.

(56) References Cited

OTHER PUBLICATIONS

Hudson et al., Engineered antibodies. Nat Med. Jan. 2003;9(1):129-34.
Janeway et al., Immunobiology, 5th ed. Garland Publishing, New York, NY. 2001. TOC only. 41 pages.
Johnston. Biolistic transformation: microbes to mice. Nature. Aug. 23, 1990;346(6286):776-7.
June. Adoptive T cell therapy for cancer in the clinic. J Clin Invest. Jun. 2007;117(6):1466-76.
Kabat et al., Sequences of Proteins of Immunological Interest. National Institutes of Health, 1991. vols. 1. TOC only. 11 pages.
Kumar et al., Biological role of lectins: A review. J. Orofac. Sci, 2012; 4: 20-25.
Lannoo et al., Lectin domains at the frontiers of plant defense. Front Plant Sci. Aug. 13, 2014;5:397. 1-16.
Lim et al., The Principles of Engineering Immune Cells to Treat Cancer. Cell. Feb. 9, 2017;168(4):724-740.
Murray. Gene Transfer and Expression Protocols. Methods in Molecular Biology, vol. 7. Humana Press. 1991. TOC only. 8 pages.
Rapoport et al., Combination immunotherapy using adoptive T-cell transfer and tumor antigen vaccination on the basis of hTERT and survivin after ASCT for myeloma. Blood. Jan. 20, 2011;117(3):788-97.
Remington: The Science and Practice of Pharmacy, Lippincott Williams & Wilkins; 21st ed. 2006. TOC only. 14 pages.
Sambrook et al., Molecular Cloning: a Laboratory Manual, 3rd ed., Cold Spring Harbor Press, Cold Spring Harbor, NY 2001. TOC only. 23 pages.
Santos et al., Lectins: Function, structure, biological properties and potential applications. Curr. Topics in Peptide and Protein Res., 2014; 15: 41-62.
Swanson et al., A lectin isolated from bananas is a potent inhibitor of HIV replication. J Biol Chem. Mar. 19, 2010;285(12):8646-55.
Swanson et al., Engineering a therapeutic lectin by uncoupling mitogenicity from antiviral activity. Cell. Oct. 22, 2015;163(3):746-58.
Woof et al., Human antibody-Fc receptor interactions illuminated by crystal structures. Nat Rev Immunol. Feb. 2004;4(2):89-99.

* cited by examiner

CHIMERIC ANTIGEN RECEPTORS TARGETING ABNORMAL GLYCOBIOLOGY

CROSS-REFERENCE TO RELATED APPLICATIONS

This application claims the benefit of U.S. Provisional Patent Application No. 62/802,001, filed Feb. 6, 2019, the disclosure of which is incorporated by reference herein.

FIELD

Chimeric antigen receptors (CARs) are provided that comprise an antigen binding domain comprising an extracellular lectin which target cells having abnormal glycobiology.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,611 Byte ASCII (Text) file named "2020-02-04_37406-202_SQL_ST25.TXT," created on Feb. 5, 2020.

BACKGROUND

Lung cancer is a devastating disease with high mortality. Treatment with cytotoxic chemotherapy and radiation can induce long term remission only in limited circumstances. The immune system plays a critical role in anti-tumor responsiveness, but activation of existing immunity is a therapeutic strategy that has had limited success in lung cancer. T cell immunity acts directly to eradicate malignancy and surveils for disease emergence and relapse. Transfer of T lymphocytes with enhanced anti-tumor activity is a promising cancer treatment, particularly as T lymphocytes can be genetically modified to confer exquisite tumor-specificity. T cells engineered to express chimeric antigen receptors (CARs), referred to as "CAR-T cells," that target specific tumors have been used successfully in the treatment of refractory B cell leukemias (Lim, W. A. & June, C. H., *Cell*, 168: 724-740 (2017)). However, the use of CAR-T cells to specifically target epithelial tumors, such as lung cancer, has been restricted by the limited number of known cancer-specific surface antigens acceptable for CAR design.

There remains a need for improved CAR polypeptides and engineered CAR-T cells with specificity and efficacy against epithelial cancers, such as lung cancer. The present disclosure provides such polypeptides and cells.

SUMMARY

Chimeric antigen receptors (CARs) are provided that comprise an antigen binding domain comprising an extracellular lectin which target cells having abnormal glycobiology. Some embodiments of the disclosure provide chimeric antigen receptor (CAR) polypeptides which comprise one or more of: an antigen binding domain comprising an extracellular lectin, a transmembrane domain (e.g., CD8α transmembrane domain), a co-stimulatory signaling domain (e.g., 4-1BB co-stimulatory signaling domain), and an intracellular signaling domain (e.g., CD3 zeta intracellular signaling domain). Also provided herein are engineered lymphocytes expressing the CAR polypeptides, a nucleic acid molecule encoding the CAR polypeptides, and a method of treating cancer using the above-described CAR polypeptides or engineered lymphocytes.

In some embodiments, provided herein are chimeric antigen receptor (CAR) polypeptides which comprises an antigen binding domain comprising an extracellular lectin, a CD8α transmembrane domain, a 4-1BB co-stimulatory signaling domain, and a CD3 zeta intracellular signaling domain. In some embodiments, the extracellular lectin is a banana lectin. In some embodiments, the banana lectin comprises an amino acid substitution. In some embodiments, a histidine (H) residue at amino acid position 84 of a wild type banana lectin comprising the amino acid sequence of SEQ ID NO: 1 is substituted with at threonine (T) residue (H84T). In some embodiments, the CAR polypeptide further comprises a hinge domain located between the antigen-binding domain and transmembrane domain. In some embodiments, the CAR polypeptide further comprises one or more linker segments located between each domain.

In some embodiments, engineered lymphocytes are provided that express one or more CAR polypeptides described herein. In some embodiments, the engineered lymphocyte is a T cell. In some embodiments, the engineered lymphocyte is a natural killer (NK) cell.

In some embodiments, nucleic acid molecules are provided comprising a nucleic acid sequence encoding one or more CAR polypeptides described herein. In some embodiments, a vector is provided comprising a nucleic acid molecule described herein. In some embodiments, an engineered lymphocyte (e.g., T cell, natural killer (NK) cell, etc.) comprising a nucleic acid molecule or vector described herein is provided.

In some embodiments, provided herein are methods of treating cancer (e.g., lung cancer) in a subject comprising administering the CAR polypeptides, nucleic acids, vectors, and/or engineered lymphocytes described herein to the subject.

In some embodiments, provided herein is the use of the CAR polypeptides, nucleic acids, vectors, and/or engineered lymphocytes described herein for the treatment of cancer (e.g., lung cancer).

DEFINITIONS

Figure 1:
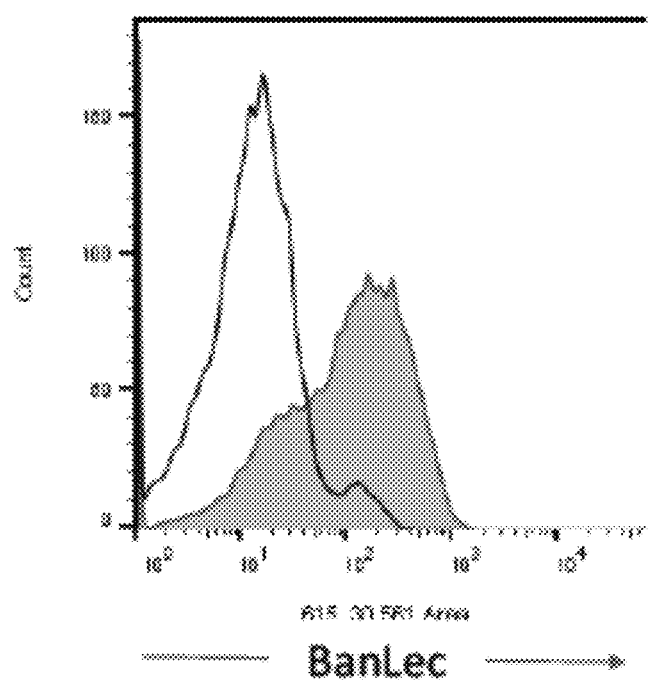
FIG. 1 is a graph illustrating the transduction efficiency of T cells modified to express the H84T BanLec-CAR as described in Example 1.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a T cell" is a reference to one or more T cells and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "antigen binding domain" refers to a molecular moiety (e.g. part of a CAR) that recognizes and binds to an antigen (e.g., antibody, antibody fragment, aptamer, receptor, cytokine, surface protein, or another antibody-based or non-antibody-based binding element). In particular embodiments, antigens can be of any nature including, but not limited to, proteins, carbohydrates, lipids, and/or synthetic molecules.

As used herein, the term "activation domain" refers to a molecular moiety (e.g. part of a CAR) that interacts with immune cells (e.g., T cell receptor (TCR)) and induces a positive or negative immunomodulatory signal. Illustrative examples of positive immunomodulatory signals include signals that induce cell proliferation, cytokine secretion, or cytolytic activity. Illustrative examples of negative immunomodulatory signals include signals that inhibit cell proliferation, inhibit the secretion of immunosuppressive factors, or induce cell death.

As used herein, the term "native immune cell" refers to an immune cell that naturally occurs in the immune system of a subject. Illustrative examples include, but are not limited to, T cells, NK cells, NKT cells, B cells, and dendritic cells.

As used herein, the term "engineered immune cell" refers to an immune cell (e.g., T cell. NK cell, NKT cell, B cell, dendritic cell, etc.) that is genetically modified.

As used herein, the term "co-stimulatory domain" or "co-stimulatory signaling domain" refers to a signaling domain of a co-stimulatory molecule. In particular aspects, it refers to a domain that provides additional signals to the immune cell in conjunction with an activation domain. Co-stimulatory molecules are cell surface molecules other than antigen receptors or Fc receptors that provide a second signal required for efficient activation and function of T lymphocytes upon binding to antigen. Illustrative examples of such co-stimulatory molecules include CD27, CD28, 4-1BB (CD137), OX40 (CD134), CD30, CD40, ICOS (CD278), LFA-1, CD2, CD7, LIGHT, NKD2C, CD70, CD80, CD86, and CD83.

The term "chimeric antigen receptor" ("CAR") refers to a recombinant polypeptide construct comprising at least an extracellular antigen binding domain, a transmembrane domain and an intracellular signaling domain. Upon binding to their target (e.g., displayed on a cancer cell), CARs typically modify the immune response of the immune cells on which they are displayed.

The term "intracellular signaling domain," when used in reference to a cell surface receptor or a CAR, is a moiety responsible for activation or inhibition of at least one function of the cell upon which the receptor or CAR is displayed. The term "effector function" refers to a specialized function of a cell. For example, effector function of a T cell includes cytolytic activity or helper activity including the secretion of cytokines. Thus, the term "intracellular signaling domain" refers to the portion of a protein which transduces the effector function signal and directs the cell to perform a specialized function. To the extent that a truncated portion or variant of a native intracellular signaling domain is active, such a polypeptide may be used in place of the full native chain, as long as it transduces the effector function signal. The term intracellular signaling domain includes any truncated or variant portion of a polypeptide sequence sufficient to transduce the effector function signal. Examples of intracellular signaling domains include the cytoplasmic sequences of the T cell receptor (TCR) and co-receptors that act in concert to initiate signal transduction following antigen receptor engagement, as well as any derivative or variant of these sequences and any synthetic sequence that has the same functional capability. Cytoplasmic signaling sequences that act in a stimulatory manner comprise signaling motifs which are known as immunoreceptor tyrosine-based activation motifs (ITAMs). Examples of ITAM-containing cytoplasmic signaling sequences include those derived from TCR zeta, FcR gamma, FcR beta, CD3 gamma, CD3 delta, CD3 epsilon, CD3 zeta, CD5, CD22, CD79a, CD79b, and CD66d.

As used herein, the term "transmembrane domain," when used in reference to a cell surface receptor or a CAR, is a moiety that spans the plasma membrane of the cell and is connected to both the intracellular signaling domain and the extracellular antigen binding domain. A transmembrane domain may be derived either from a natural or from a synthetic source. Where the source is natural, the domain may be derived from any membrane-bound or transmembrane protein, for example, the alpha, beta or zeta chain of the T cell receptor, CD28, CD3 epsilon, CD45, CD4, CD5, CD8, CD9, CD16, CD22, CD33, CD37, CD64, CD80, CD86, CD134, CD137, CD154, etc. Alternatively, the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the intracellular signaling domain. A glycine-serine doublet provides a particularly suitable linker.

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (e.g., antibodies, cytokines, and complement) that results in selective targeting, binding to, damage to, destruction of, and/or elimination from a subject of invading pathogens, cells or tissues infected with pathogens, or cancerous cells or other abnormal/diseased-associated cells.

As used herein, the term "immunotherapy" refers to the treatment or prevention of a disease or condition by a method comprising inducing, enhancing, suppressing or otherwise modifying an immune response.

As used herein, the term "adoptive cell transfer" ("ACT") is the transfer of cells into a patient. The cells may have originated from the patient or from another individual or cell line. The cells are most commonly derived from the immune system, with the goal of improving immune functionality or eliciting a desired immune response. In some embodiments, cells are extracted from a subject, genetically modified (e.g., to express a desired construct (e.g., CAR or endanger molecule)), cultured in vitro, and returned to the subject.

As used herein, the term "antibody" refers to a whole antibody molecule or a fragment thereof (e.g., fragments such as scFv, Fab, Fab', and F(ab')$_2$), unless specified otherwise; an antibody may be a polyclonal or monoclonal antibody, a chimeric antibody, a humanized antibody, a human antibody, etc. In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen binding site. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) *J. Mol. Biol.*, 196:901-917; or Chothia, C. et al. *Nature.* 342:878-883 (1989). In the present application, the term "CDR" refers to a CDR from either the light or heavy chain, unless otherwise specified.

As used herein, when an antibody or other entity (e.g., antigen binding domain) "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ M$^{-1}$ (e.g., >$10^7$ M$^{-1}$, >$10^8$ M$^{-1}$, >$10^9$ M$^{-1}$, >$10^{10}$ M$^{-1}$, >$10^{11}$ M$^{-1}$, >$10^{12}$ M$^{-1}$, >$10^{13}$ M$^{-1}$, etc.). In certain such embodiments, an antibody is capable of binding different antigens so long as the different antigens comprise that particular epitope. In certain instances, for example, homologous proteins from different species may comprise the same epitope.

As used herein, the term "antibody fragment" refers to a portion of a full-length antibody, including at least a portion antigen binding region or a variable region. Antibody fragments include, but are not limited to, Fab, Fab', F(ab')$_2$, Fv, scFv, Fd, diabodies, and other antibody fragments that retain at least a portion of the variable region of an intact antibody (see. e.g., Hudson et al., *Nat. Med.*, 9: 129-134 (2003)). In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab')$_2$" molecule. An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen binding region. Exemplary single chain antibodies are discussed in detail in WO 88/01649 and U.S. Pat. Nos. 4,946,778 and 5,260,203. In certain instances, a single variable region (e.g., a heavy chain variable region or a light chain variable region) may have the ability to recognize and bind antigen. Other antibody fragments will be understood by skilled artisans.

The term "antigen binding site" refers to a portion of an antibody capable of specifically binding an antigen. In certain embodiments, an antigen binding site is provided by one or more antibody variable regions.

A "lectin" is a carbohydrate-binding protein which is widely found in nature, particularly plants. Lectins are highly specific for sugar moieties of other molecules and mediate attachment and binding of bacteria and viruses to target molecules in cells. Lectins have been used in many aspects of glycobiology (Andre' et al., *Molecules*, 20: 1788-1823 (2015): Gabius et al., Trends Biochem. Sci., 36(6): 298-313 (2011), and Gabius et al., *Trends Biochem. Sci.*, 40: 360-376 (2015)), including as potential antiviral agents.

The term "epitope" refers to any polypeptide determinant capable of specifically binding to an immunoglobulin, a T cell or B cell receptor, or any interacting protein, such as a surface protein. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three-dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position. In some embodiments, peptides or polypeptides herein comprise a minimum sequence identity to a base sequence.

As used herein, the terms "administration" and "administering" refer to the act of giving a drug, prodrug, therapeutic, or other agent to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

The present disclosure is predicated, at least in part, on the development of chimeric antigen receptor (CAR) polypeptides that specifically binds to cells which exhibit altered glycobiology at the cell surface. For example, lung tumors typically exhibit disordered glycan assembly. CARs targeting aberrant glycans have thus far been antibody (e.g., scFv) based, with their efficacy wholly dependent on the binding properties of the scFv-derived extracellular binding moiety. The CAR polypeptides described herein may be used to target cancer cells, such as lung cancer, displaying aberrant glycosylation patterns which thus far have been difficult to target using conventional scFv-based CARs.

I. CARs

In some embodiments, the CAR polypeptide comprises an extracellular domain having an antigen binding domain, a transmembrane domain, and a cytoplasmic domain having an intracellular signaling domain and a co-stimulatory signaling domain. In some embodiments, the CAR further comprises a hinge domain (e.g., extracellular or intracellular hinge) or other linker between domains.

The extracellular domain of the CAR described herein comprises an antigen binding domain. The choice of antigen binding domain depends upon the type and number of ligands that define the surface of a target cell. For example, the antigen binding domain may be chosen to recognize a ligand that acts as a cell surface marker on target cells associated with a particular disease state. Cell surface markers that may act as ligands for the antigen binding domain in the CAR of include antigens or proteins associated with viral, bacterial and parasitic infections, or antigens or proteins expressed by diseased cells (e.g., autoimmune disease and cancer).

In some embodiments, the CAR targets cancer cells by displaying an antigen binding domain that specifically binds to an antigen expressed on a cancer cell. The terms "cancer-specific antigen (CSA)" and "tumor-specific antigen (TSA)" are used interchangeably herein and refer to a protein, carbohydrate, or other molecule that is uniquely expressed by and/or displayed on cancer cells and is not expressed by or displayed on other cells in the body (e.g., normal healthy cells). In contrast, the terms "cancer-associated-antigen (CAA)" and "tumor-associated-antigen (TAA)" are used interchangeably herein and refer to a protein, carbohydrate, or other molecule that is not uniquely expressed by or displayed on a tumor cell and instead is also expressed on normal cells under certain conditions.

The selection of the antigen binding domain depends on the particular type of cancer to be treated. Cancer-specific antigens and cancer-associated antigens are well known in the art. In some embodiments, the CSA or CAA comprises one or more antigenic cancer epitopes associated with a malignant cancer or tumor, a metastatic cancer or tumor, or a leukemia. In one embodiment, the CAR polypeptide comprises an antigen binding domain that specifically binds glycoproteins expressed on the surface of target cells. In particular embodiments, the antigen binding domain of the disclosed CAR comprises an extracellular lectin. A lectin is "extracellular" in that it interacts with carbohydrates expressed at the cell surface. The antigen binding domain may comprise any suitable lectin protein known in the art, such as those described in, e.g., Santos et al., *Curr. Topics in Peptide and Protein Res.*, 15: 41-62 (2014); and Kumar et al., *J. Orofac. Sci*, 4: 20-25 (2012). In some embodiments, the extracellular lectin is obtained or derived from a banana plant (referred to herein as "BanLec"). BanLec is a jacalin-related lectin isolated from the fruit of bananas, *Musa acuminata*. BanLec binds to high mannose carbohydrate structures, including those found on viruses containing glycosylated envelope proteins such as human immunodeficiency virus type-1 (HIV-1) (Swanson et al., *J. Biol. Chem.*, 285(12): 8646-55 (2010)). An exemplary naturally occurring banana lectin amino acid sequence comprises SEQ ID NO: 1. As discussed above, lectins have the potential to be used as antiviral agents, but clinical applications of lectins suffer from possible side effects mediated by lectin-induced mitogenicity (Borrebaeck. A. K., and Carlsson, R., *Adv. Lectin Res.*, 2: 1-27 (1989)). A single amino acid substitution in BanLec, however, significantly reduces the mitogenic effects of BanLec while preserving carbohydrate binding (Swanson et al., *Cell*, 163(3): 746-58 (2015)). In some embodiments, the antigen binding domain of the disclosed CAR comprises a banana lectin having the amino acid sequence of SEQ ID NO: 2, in which the histidine (H) residue at amino acid position 84 of SEQ ID NO: 1 is substituted with a threonine (T) residue. In other embodiments, the antigen binding domain comprises 70% or greater (e.g., 70%, 75%, 80%, 85%, 90%, 95%, 100%, or ranges therebetween) amino acid sequence identity with SEQ ID NO: 2 or a portion thereof (e.g., a portion 25 amino acids in length or greater (e.g., 25 amino acids, 50 amino acids, 75 amino acids, 100 amino acids, or more, or ranges therebetween).

The CAR polypeptide described herein comprises a transmembrane domain. CARs typically are designed to comprise a transmembrane domain that is fused to the extracellular and intracellular domains of the CAR. In some embodiments, a transmembrane domain is a sequence that is naturally associated with one of the other domains in the CAR. In other embodiments, the transmembrane domain is selected or modified by amino acid substitution to avoid interactions with other CAR domains or cell surface components.

In some embodiments, a transmembrane domain is obtained or derived from a natural or a synthetic source. Where the source is natural, the domain may be derived from any membrane-bound or transmembrane protein. Transmembrane regions of particular use include at least the transmembrane region(s) of known transmembrane proteins, including, but not limited to: the alpha, beta or zeta chain of the T cell receptor, CD8ac, CD28, CD3 epsilon, CD45, CD4, CD5, CDS, CD9, CD 16, CD22, CD33, CD37, CD64, CD80, CD86, CD 134, CD137, CD 154. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic domain of the CAR. A glycine-serine doublet provides a particularly suitable linker. In some embodiments, the disclosed CAR comprises a CD8α transmembrane domain.

The cytoplasmic domain (also referred to as the intracellular signaling domain, activation domain, etc.) of the CAR is responsible for activation of at least one of the normal effector functions of the immune cell in which the CAR has been introduced. As described above, the term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While the entire intracellular signaling domain of a known protein or protein complex may be employed in certain embodiments, in other embodiments it is not necessary to use the entire chain. To the extent that a truncated portion of a known intracellular signaling domain is used, such truncated portion may be used in place of the intact chain as long as it transduces the effector function signal. Examples of intracellular signaling domains for use in the CARs herein include the cytoplasmic sequences of the T cell receptor (TCR) and co-receptors that act in concert to initiate signal transduction following antigen-receptor engagement, as well as any derivative or variant of these sequences and any synthetic sequence that has the same functional capability.

In some embodiments, signals generated through the TCR alone are insufficient for full activation of the T cell. In such cases, a secondary or co-stimulatory signal also is required for full activation. Thus, in some embodiments, T cell activation is mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences). Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the invention include those derived from TCR zeta, FcR gamma, FcR beta, CD3 gamma. CD3 delta, CD3 epsilon, CDS, CD22, CD79a, CD79b, and CD66d. In some embodiments, the disclosed CAR comprises an intracellular (cytoplasmic) signaling domain derived from CD3 zeta.

In some embodiments, the cytoplasmic domain of the CAR comprises a primary signaling sequence (e.g., CD3 zeta signaling domain) alone or in combination with any other desired cytoplasmic domain(s) useful in the context of the CAR. In some embodiments, as described above, the cytoplasmic domain of the CAR may comprise a primary signaling sequence and a co-stimulatory signaling domain. Any suitable co-stimulatory signaling domain may be used in the inventive CAR. Such co-stimulatory domains are present in, for example, CD27, CD28, 4-1BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83. In one embodiment, the CAR may comprise a 4-1BB co-stimulatory signaling domain in combination with a CD3 zeta intracellular signaling domain.

The cytoplasmic signaling sequences within the cytoplasmic signaling portion of the CAR may be linked to each other in a random or specified order. Optionally, a short oligopeptide linker (e.g., between 2 and 25 amino acids in length) may form the linkage. A glycine-serine doublet provides a particularly suitable linker.

Between the extracellular domain and the transmembrane domain of the CAR, or between the cytoplasmic domain and the transmembrane domain of the CAR, there may be incorporated a linker domain. A linker domain of a CAR is an oligo- or polypeptide that functions to link the transmembrane domain to, either the extracellular domain or, the cytoplasmic domain in the polypeptide chain. A linker domain may comprise up to 300 amino acids (e.g., 1, 2, 5, 10, 20, 30, 40, 50, 75, 100, 125, 150, 200, 250, 300, or ranges therebetween (e.g., 10 to 100 amino acids, 25 to 50 amino acids, etc.)).

In another embodiment, the CAR comprises a hinge sequence, which is a short amino acid sequence that promote flexibility of the antigen binding domain (see, e.g., Woof et al., *Nat. Rev. Immunol.*, 4(2): 89-99 (2004)). The hinge sequence may be positioned between the antigen binding domain and the transmembrane domain. The hinge sequence can be any suitable sequence derived or obtained from any suitable molecule. In one embodiment, for example, the hinge sequence is derived from the human CD8α molecule or a CD28 molecule.

While a variety of CARs comprising various combinations of antigen binding domains, transmembrane domains, and intracellular signaling domains are encompassed by embodiments herein, particular embodiments herein comprise CARs having: (a) an antigen binding domain that recognizes and specifically binds to cell surface glycoproteins (e.g., an extracellular lectin such as BanLec), (b) a transmembrane domain comprising all or a portion of the transmembrane domain of CD8a; and (c) an intracellular signaling domain comprising all or a portion of the intracellular signaling domain of CD3 zeta and a co-stimulatory signaling domain comprising all or a portion of the intracellular signaling domain of 4-1BB.

II. Cells, Nucleic Acids, and Vectors

Provided herein are nucleic acid molecules and nucleic acid sequences encoding the above-described CARs and lymphocytes engineered to contain and express such nucleic acid sequences. Nucleic acids encoding CARs may comprise DNA, RNA, PNA (peptide nucleic acid), and hybrids thereof. In some embodiments, a nucleic acid encoding a CAR comprises one or more regulatory sequences. For example, promoters, transcriptional enhancers and/or sequences that allow for induced expression of the polynucleotide of the disclosure may be employed.

The nucleic acid sequence can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual*, 3rd ed., Cold Spring Harbor Press, Cold Spring Harbor, NY 2001, and Ausubel et al., *Current Protocols in Molecular Biology*, Greene Publishing Associates and John Wiley & Sons, N Y. 1994). Further, a synthetically produced nucleic acid sequence encoding the CAR can be isolated and/or purified from a source, such as a plant, a bacterium, an insect, or a mammal, e.g., a rat, a human, etc. Methods of isolation and purification are well-known in the art. Alternatively, the nucleic acid sequences described herein can be commercially synthesized. In this respect, the inventive nucleic acid sequence can be synthetic, recombinant, isolated, and/or purified.

In one embodiment, the disclosure provides a nucleic acid sequence encoding a CAR that comprises or consists of the amino acid sequence of SEQ ID NO: 2. For example, the nucleic acid sequence may comprise SEQ ID NO: 3.

Also provided herein is a vector comprising the nucleic acid sequence encoding the CAR described herein. The vector can be, for example, a plasmid, a cosmid, a viral vector (e.g., retroviral or adenoviral), or a phage. Suitable vectors and methods of vector preparation are well known in the art (see, e.g., Sambrook et al., supra, and Ausubel et al., supra). In one embodiment, the vector is a viral vector. Representative viral expression vectors include, but are not limited to, adenovirus-based vectors, adeno-associated virus (AAV)-based vectors, lentivirus-based vectors, and retroviral vectors. In a specific embodiment, the viral vector is a lentivirus vector. Alternatively, the nucleic acid sequence and vectors of the disclosure may be reconstituted into liposomes for delivery to target cells.

A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In some embodiments, a vector comprises a nucleic acid sequence that is a regulatory sequence operably linked to the nucleic acid sequence encoding a CAR described herein. Such regulatory sequences (control elements) are known to the ordinarily skilled artisan and may include a promoter, a splice cassette, translation initiation codon, insertion site for introducing an insert into the vector, and polyadenylation sequences. In specific embodiments, the nucleic acid molecule is operatively linked to expression control sequences (e.g., a promoter), allowing expression in eukaryotic or prokaryotic cells.

The nucleic acid molecule and/or vector described above may be introduced a cell capable of expressing the CAR encoded thereby. The cell can be a eukaryotic cell, e.g., plant, animal, fungi, or algae, or can be a prokaryotic cell, e.g., bacteria or protozoa. The cell can be a cultured cell or a primary cell, i.e., isolated directly from an organism, e.g., a human. In certain embodiments, a vector or nucleic acid molecule encoding the CAR is introduced into lymphocytes, so as to produce engineered lymphocytes which express or display one or more chimeric antigen receptors (CARs) as described herein. Methods for selecting suitable lymphocytes and methods for transformation, culture, amplification, screening, and purification of such cells are known in the art. In specific embodiments, the engineered lymphocytes may be selected from T cells, natural killer (NK) cells, natural killer T (NKT) cells, B cells, dendritic cells, and the like.

In one embodiment, the engineered lymphocyte is a T cell, such as a cultured T cell or a T cell obtained directly from a mammal (e.g., a human). If obtained from a mammal, the T cell can be obtained from numerous sources, including but not limited to blood, bone marrow, lymph node, the thymus, or other tissues or fluids. T cells can also be enriched for or purified. The T cell desirably is a human T cell. The T cell can be of any developmental stage, including but not limited to, a $CD4^+/CD8^+$ double positive T cell, a CD4+ helper T cell, e.g., Th, and Th2 cells, a CD8+T− cell (e.g., a cytotoxic T cell), a tumor infiltrating cell, a memory T cell, a naive T cell, and the like. In one embodiment, the T cell is a CD8+ T cell or a CD4+ T cell. T cell lines are available from, e.g., the American Type Culture Collection (ATCC, Manassas, VA), and the German Collection of Microorganisms and Cell Cultures (DSMZ) and include, for example, Jurkat cells (ATCC TIB-152), Sup-TI cells (ATCC CRL-1942), RPMI 8402 cells (DSMZ ACC-290), Karpas 45 cells (DSMZ ACC-545), and derivatives thereof. T cells which express CARS are referred to in the art as "CAR T cells," "CAR-T cells," or "CART cells."

In another embodiment, the engineered lymphocyte is a natural killer (NK) cell. NK cells are a type of cytotoxic lymphocyte that plays a role in the innate immune system. NK cells are defined as large granular lymphocytes and constitute the third kind of cells differentiated from the common lymphoid progenitor which also gives rise to B and T lymphocytes (see, e.g., Immunobiology, 5th ed., Janeway et al., eds., Garland Publishing, New York, NY (2001)). NK cells differentiate and mature in the bone marrow, lymph node, spleen, tonsils, and thymus. Following maturation, NK cells enter into the circulation as large lymphocytes with distinctive cytotoxic granules. NK cells are able to recognize and kill some abnormal cells, such as, for example, some tumor cells and virus-infected cells, and are thought to be important in the innate immune defense against intracellular pathogens. As described above with respect to T cells, the NK cell can a cultured NK cell or an NK cell obtained directly from a mammal. If obtained from a mammal, the NK cell can be obtained from numerous sources, including but not limited to blood, bone marrow, lymph node, the thymus, or other tissues or fluids. NK cells can also be enriched for or purified. The NK cell desirably is a human NK cell. NK cell lines are available from, e.g., the American Type Culture Collection (ATCC, Manassas, VA) and include, for example, NK-92 cells (ATCC CRL-2407), NK92MI cells (ATCC CRL-2408), and derivatives thereof.

The above-described vectors or nucleic acid molecules encoding a CAR may be introduced into a cell (e.g., a lymphocyte) by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.). Methods in Molecular Biology, Vol. 7, Gene Transfer and Expression Protocols, Humana Press (1991)), DEAE-dextran, electroporation, cationic liposome-mediated transfection, tungsten particle-facilitated microparticle bombardment (Johnston, Nature, 346: 776-777 (1990)), and strontium phosphate DNA co-precipitation (Brash et al., Mol. Cell Biol., 7: 2031-2034 (1987)). Phage or viral vectors can be introduced into host cells after growth of infectious particles in suitable packaging cells, many of which are commercially available. The nucleic acid molecule or vector that is introduced in a host cell may either integrate into the genome of the host or it may be maintained extrachromosomally.

In some embodiments, nucleic acids encoding the CAR polypeptides are inserted into the genetic material of a host cell (e.g., a lymphocyte) using a CRISPR/Cas9 system. CRISPRs are DNA loci comprising short repetitions of base sequences. Each repetition is followed by short segments of "spacer DNA" from previous exposures to a virus. CRISPRs are often associated with Cas genes that code for proteins related to CRISPRs.

The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system may be used for gene editing. By delivering the Cas9 protein and appropriate guide RNAs into a cell, the organism's genome can be cut at any desired location. Methods for using CRISPR/Cas9 systems, and other systems, for insertion of a gene into a host cell to produce an engineered cell are described in, for example, U.S. Patent Application Publication 2018/0049412.

III. Treatments and Therapeutics

Without being bound to a particular theory or mechanism, it is believed that by specifically binding to altered glycoproteins expressed on the surface of certain types of cancer cells (e.g., lung cancer), the CARs described herein provide for one or more of the following: targeting and destroying glycoprotein-expressing cancer cells, reducing or eliminating cancer cells, facilitating infiltration of immune cells to tumor site(s), and enhancing/extending anti-cancer responses. Thus, in various embodiments, the CARs, nucleic acid sequences, vectors, engineered lymphocytes, etc. as contemplated herein and/or pharmaceutical compositions comprising the same are used for the prevention, treatment or amelioration of a cancerous disease, such as, for example lung cancer. For example, the disclosure provides a method of treating cancer in a subject in need thereof (e.g., a human) comprising administering the engineered lymphocytes, CARs, nucleic acid molecules, or vectors described herein to the subject. The disclosure also provides the use of the engineered lymphocytes, CARs, nucleic acid molecules, or vectors described herein for the treatment of cancer (e.g., lung cancer).

In some embodiments, one or more isolated engineered lymphocytes expressing a nucleic acid sequence encoding the BanLec-specific CAR described herein can be contacted with a population of cancer cells that express lectin-binding glycoproteins ex vivo, in vivo, or in vitro. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context. The method desirably involves ex vivo and in vivo components. In this regard, for example, the isolated engineered lymphocytes described above can be cultured ex vivo under conditions to express the nucleic acid sequence encoding the BanLec-specific CAR, and then directly transferred into a mammal (preferably a human) suffering from cancer (e.g., lung cancer). Such a cell transfer method is referred to in the art as "adoptive cell transfer (ACT)," in which immune-derived cells are passively transferred into a new recipient host to transfer the functionality of the donor immune-derived cells to the new host.

Adoptive cell transfer methods to treat various types of cancers are known in the art and disclosed in, for example, Gattinoni et al., *Nat. Rev. Immunol*, 6(5): 383-393 (2006); June, C H, *J. Clin. Invest.*, 117(6): 1466-76 (2007); Rapoport et al., *Blood*, 117(3): 788-797 (2011); and Barber et al., *Gene Therapy*, 18: 509-516 (2011)).

When T cells or NK cells are administered to a mammal, the cells can be allogeneic or autologous to the mammal. In "autologous" administration methods, cells (e.g., lymphocytes) are removed from a mammal, stored, engineered or modified (as described herein) and returned back to the same mammal. In "allogeneic" administration methods, a mammal receives cells (e.g., blood-forming stem cells or lymphocytes) from a genetically similar, but not identical, donor. Ideally, the cells are autologous to the mammal.

Engineered lymphocytes, CARs, nucleic acid molecules, and vectors, as described herein, can be formulated into a composition, such as a pharmaceutical composition, and administered to a human. For example, the pharmaceutical composition can comprise a population of T cells of NK cells that express the CAR. When cells are administered in a composition or formulation, the engineered cells are either administered to a site of treatment or may localize at a site of treatment (e.g., cell type, tissue type, etc.).

The pharmaceutical composition desirably comprises a carrier, such as a pharmaceutically acceptable carrier. The choice of carrier will be determined in part by the particular nucleic acid molecule, vector, or lymphocytes expressing the CAR, as well as by the particular method used to administer the nucleic acid molecule, vector, or lymphocytes expressing the CAR. For example, the pharmaceutical composition may contain preservatives, such as, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition. In addition, buffering agents may be used in the composition. Suitable buffering agents include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition. Methods for preparing administrable (e.g., parenterally administrable) compositions are known to those skilled in the art and are described in more detail in, for example, Remington: *The Science and Practice of Pharmacy*, Lippincott Williams & Wilkins; 21st ed. (May 1, 2005).

In some embodiments, the composition can employ time-released, delayed release, and sustained release delivery systems such that the delivery of the composition occurs prior to, and with sufficient time to cause, sensitization of the site to be treated. Many types of release delivery systems are available and known to those of ordinary skill in the art. Such systems can avoid repeated administrations of the composition, thereby increasing convenience to the subject and the physician, and may be particularly suitable for certain embodiments.

The composition desirably comprises the engineered lymphocytes, the nucleic acid sequence encoding a CAR, or a vector comprising the nucleic acid sequence, in an amount that is effective to treat or prevent certain types of cancer (e.g., lung cancer). As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the method comprises administering a "therapeutically effective amount" of the composition comprising engineered lymphocytes expressing the nucleic acid sequence encoding a CAR, the CAR polypeptide itself, or a vector comprising the nucleic acid sequence. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the CAR to elicit a desired response in the individual. For example, a therapeutically effective amount of CAR of the invention is an amount which binds to altered glycoproteins on the surface of cancer cells and destroys the cancer cells.

Alternatively, the pharmacologic and/or physiologic effect may be prophylactic, i.e., the effect completely or partially prevents a disease or symptom thereof. In this respect, the method comprises administering a "prophylactically effective amount" of the composition comprising engineered lymphocytes expressing the nucleic acid sequence encoding a CAR, the CAR polypeptide itself, or a vector comprising the nucleic acid sequence, to a mammal (e.g., a human) that is predisposed to cancer. A "prophylactically effective amount" refers to an amount effective, at dosages and for periods of time necessary, to achieve a desired prophylactic result (e.g., prevention of disease onset).

A typical amount of cells (e.g., engineered lymphocytes) administered to a mammal (e.g., a human) can be, for example, in the range of one million to 100 billion cells; however, amounts below or above this exemplary range are within the scope of the disclosure. For example, the daily dose of cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), preferably about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), more preferably about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the disclosure. The desired dosage can be delivered by a single bolus administration of the composition, by multiple bolus administrations of the composition, or by continuous infusion administration of the composition.

The composition comprising the engineered lymphocytes expressing a CAR-encoding nucleic acid sequence, the CAR polypeptide itself, or a vector comprising the nucleic acid sequence, can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

As discussed above, indications for administration of the composition(s) herein desirably are cancerous diseases, particularly epithelial cell cancers exhibiting abnormal glycobiology (e.g., disordered glycan assembly on the cell surface). Examples of such cancers include, but are not limited to, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma. CNS lymphoma, germinoma, medulloblastoma. Schwannoma craniopharyogioma, ependymoma, pineaioma, hemangioblastoma, acoustic neuroma, oligodendroglioma, menangioma, neuroblastoma, retinoblastoma and brain metastases). In one embodiment, the cancer is a lung cancer (e.g., non-small cell lung cancer, small cell lung cancer, or lung carcinoid tumors).

In other embodiments, the compositions described herein may be administered to a subject suffering from a hematological cancer. Examples of hematological cancers that may be treated by the methods disclosed herein include, but are not limited to, leukemias, including acute leukemias (such as acute lymphocytic leukemia, acute myelocytic leukemia, acute myelogenous leukemia and myeloblasts, promyciocytic, myclomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukemia, and myelodysplasia.

In other embodiments, the compositions described herein may be used to treat a viral infection. As discussed above, BanLec binds to high mannose carbohydrate structures found on viruses containing glycosylated envelope proteins, such as human immunodeficiency virus type-1 (HIV-1). Thus, it is believed that BanLec also binds HIV-infected T cells that display the viral envelope on their surface. The disclosed compositions may be administered to a subject (e.g., a human) infected with any virus, including but not limited to HIV, human papilloma virus (HPV), influenza virus, herpes viruses, hepatitis viruses, and the like.

The disclosure further encompasses co-administration protocols with other compounds, e.g., bispecific antibody constructs, targeted toxins or other blocking or functional antibodies or compounds, which act via immune cells. The clinical regimen for co-administration may encompass co-administration at the same time, before or after the administration of the other component. Particular combination therapies include chemotherapy, radiation, surgery, hormone therapy, or other types of immunotherapy. Many chemotherapeutics are presently known in the art and can be used in combination with the disclosed CARs. In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Specific chemotherapeutic agents include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabine, fuldarabine, navelbine, farnesyl-protein tansferase inhibitors, transplatinum, 5-fluorouracil, vincristin, and vinblastin, or any analog or derivative variant of the foregoing and also combinations thereof. In some embodiments, chemotherapy is employed before, during and/or after administration of engineered lymphocytes or other compositions described herein.

In some embodiments, the engineered lymphocytes or other compositions described herein are co-administered with radiotherapy, methods of which are understood in the field. In some embodiments, radiotherapy is employed before, during and/or after administration of or other compositions described herein.

In some embodiments, the engineered lymphocytes or other compositions described herein are co-administered with non-immune based targeted therapies, such as, agents that inhibit signaling pathways such WNT, p53, and/or RB-signaling pathways. Other examples include agents that inhibit tyrosine kinases, BRAF, STAT3, c-met, regulate gene expression, induce cell death or block blood vessel formation. Examples of specific agents include imatinib mesylate, dasatinib, nilotinib, bosutinib, lapatinib, gefinitib, erlotinib, tensirolimus, everolimus, vemurafenib, crizotinib, vorinostat, romidepsin, bexarotene, alitrionin, tretionin, bortezomib, carfilzomib, pralatrexate, sorafenib, sunitinib, pazopanib, regorafenib, or cabozantinib. In some embodiments, non-immune based targeted therapy is employed before, during and/or after administration of or other compositions described herein.

In some embodiments, the engineered lymphocytes or other compositions described herein are co-administered with an immunotherapy. Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect-cell killing. The antibody may also prevent cancer immunoevasion or immunosuppression. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells, NKT cells, and NK cells. In some embodiments, immunotherapy is employed before, during and/or after administration of or other compositions described herein. In some embodiments, engineered lymphocytes are co-administered with an immune checkpoint inhibitor (e.g., anti-PD1, anti-PDL1, anti-CTLA-4, etc.).

In some embodiments, the engineered lymphocytes or other compositions described herein are co-administered with a gene therapy in which a therapeutic polynucleotide is administered before, after, or at the same time as the engineered lymphocytes described herein. A variety of expression products are encompassed, including inducers of cellular proliferation, inhibitors of cellular proliferation, or regulators of programmed cell death.

In some embodiments, the engineered lymphocytes or other compositions described herein are administered before, during, and/or after surgery. Surgeries include resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that embodiments herein may be used in conjunction with removal of superficial cancers, precancers, or incidental amounts of normal tissue.

In some embodiments, the engineered lymphocytes or other compositions described herein are co-administered with other agents to improve the therapeutic efficacy of treatment.

In some embodiments, engineered lymphocytes or other compositions described herein are provided as part of a kit or system along with one or more additional components, such as instructions, devices for administration, additional therapeutic agents, diagnostic agents, research agents, etc.

The following examples further illustrate the invention but, of course, should not be construed as in any way limiting its scope.

Example 1

This example describes the generation of BanLec-expressing CAR-T cells.

An expression cassette containing the coding sequence for H84T BanLec, a short hinge region, the transmembrane domain of CD8a, and the intracellular portions of 4-1BB and CD3 zeta was designed and subcloned into a standard retroviral vector. Replication incompetent retrovirus was produced by transient transfection of 293T cells with a packaging and envelope plasmid. Primary peripheral blood mononuclear cells were obtained by Ficoll gradient and T cells activated on αCD3 and αCD28 coated tissue culture plates. Transduction was carried out with virus immobilization on retronectin and subsequent layering of activated T cells. CAR expression was assessed by FACS following 5-7 days of culture. Cells were stained first with an antibody specific to BanLec and then with a secondary antibody conjugated to a fluorophore (see FIG. 1).

Example 2

This example describes experiments for functional ex vivo testing of BanLec-CAR T cells.

Figure 2:
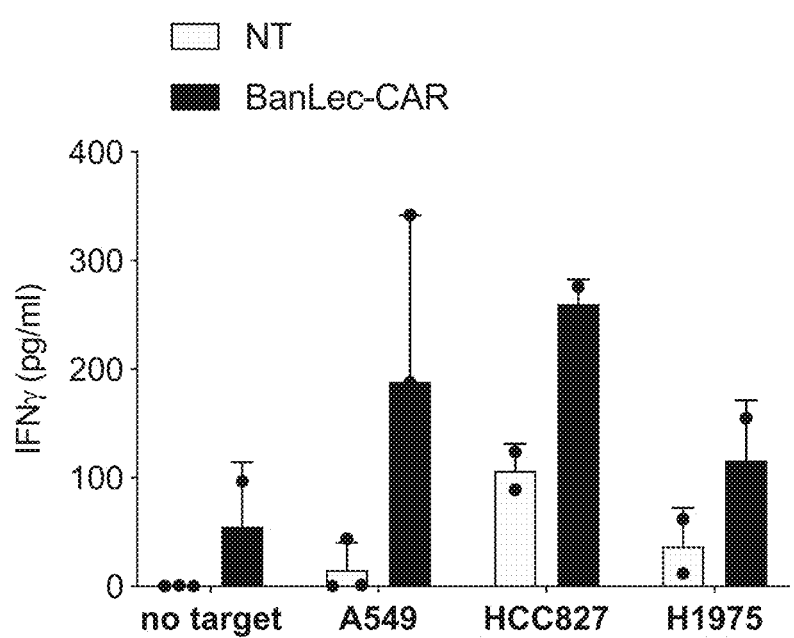
FIG. 2 is a graph illustrating interferon-gamma (IFNγ) production by lung cancer cell lines cultured in the presence unmodified T cells (NT) or H84T BanLec-CAR T cells.

Unmodified T cells and the BanLec-CART cells produced in Example 1 were plated at a 1:1 effector:target ratio with the lung cancer cell lines A549, HCC827, and H1975. After 24 hours of culture, supernatant was collected and evaluated for the presence of interferon-gamma (IFNγ) as an indicator of T cell activation. H84T BanLec-CART cells exhibited specific anti-lung tumor activity, as shown in FIG. 2.

Figure 3A:
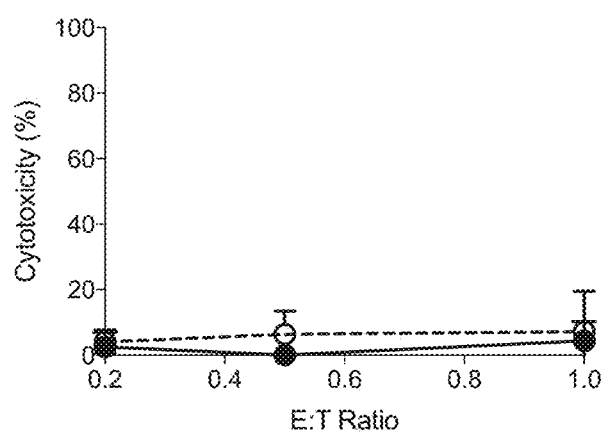
FIG. 3A is a graph illustrating cytotoxicity of H84T BanLec-CAR T cells and unmodified T cells (NT) against the leukemia MV411 cell line.
Figure 3B:
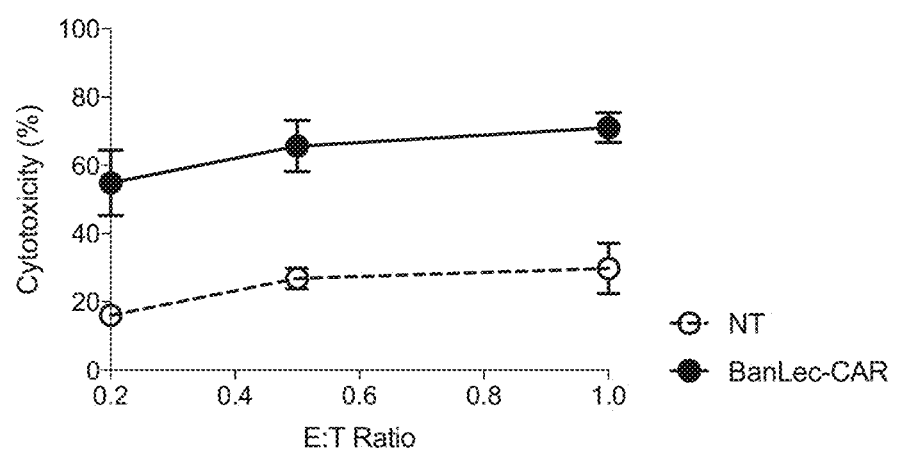
FIG. 3B is a graph illustrating cytotoxicity of H84T BanLec-CAR T cells and unmodified T cells against A549 lung cancer cells in vitro.
Figure 4A:
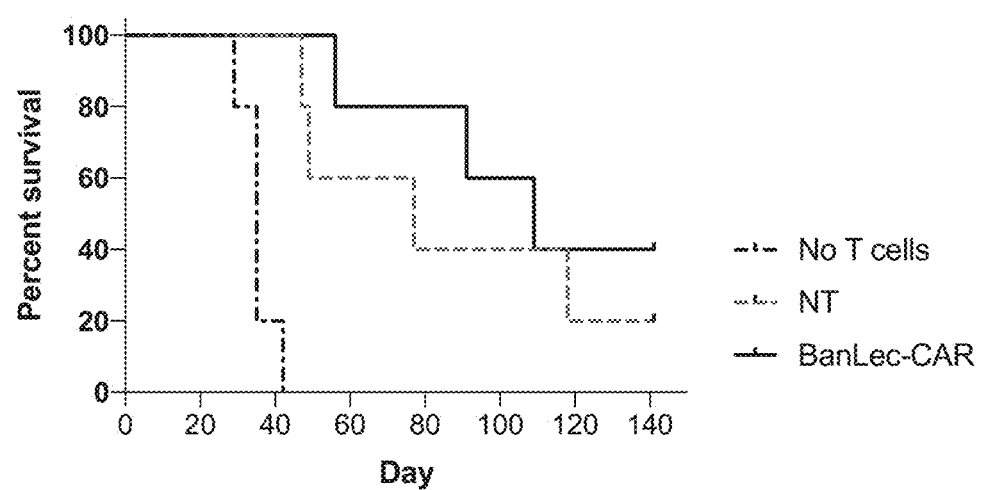
FIG. 4A is a graph illustrating survival in a mouse xenograft model of lung cancer treated with H84T BanLec-CAR T cells as compared to treatment with unmodified T cells (NT) or no T cells.
Figure 4B:
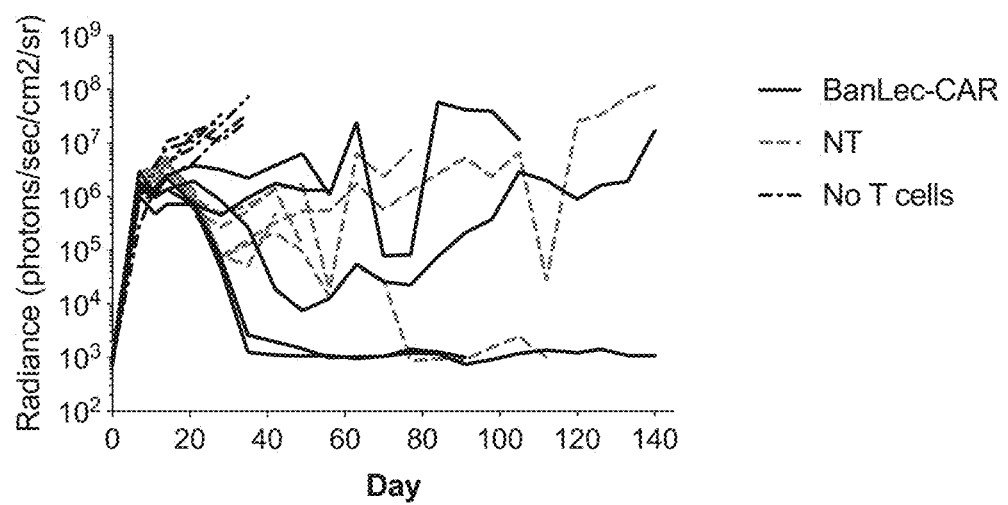
FIG. 4B is a graph illustrating lung cancer growth (indicated by bioluminescence as lung cancer cell lines are engineered to express firefly Luciferase which facilitates light emission after mice are injected with D-Luciferin).
Figure 4C:
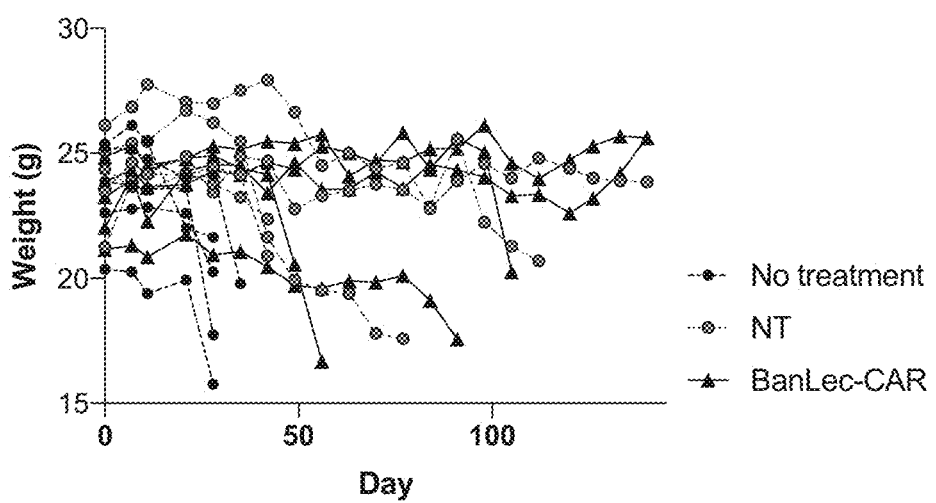
FIG. 4C is a graph showing mouse body weights during the treatment period.
Figure 4D:
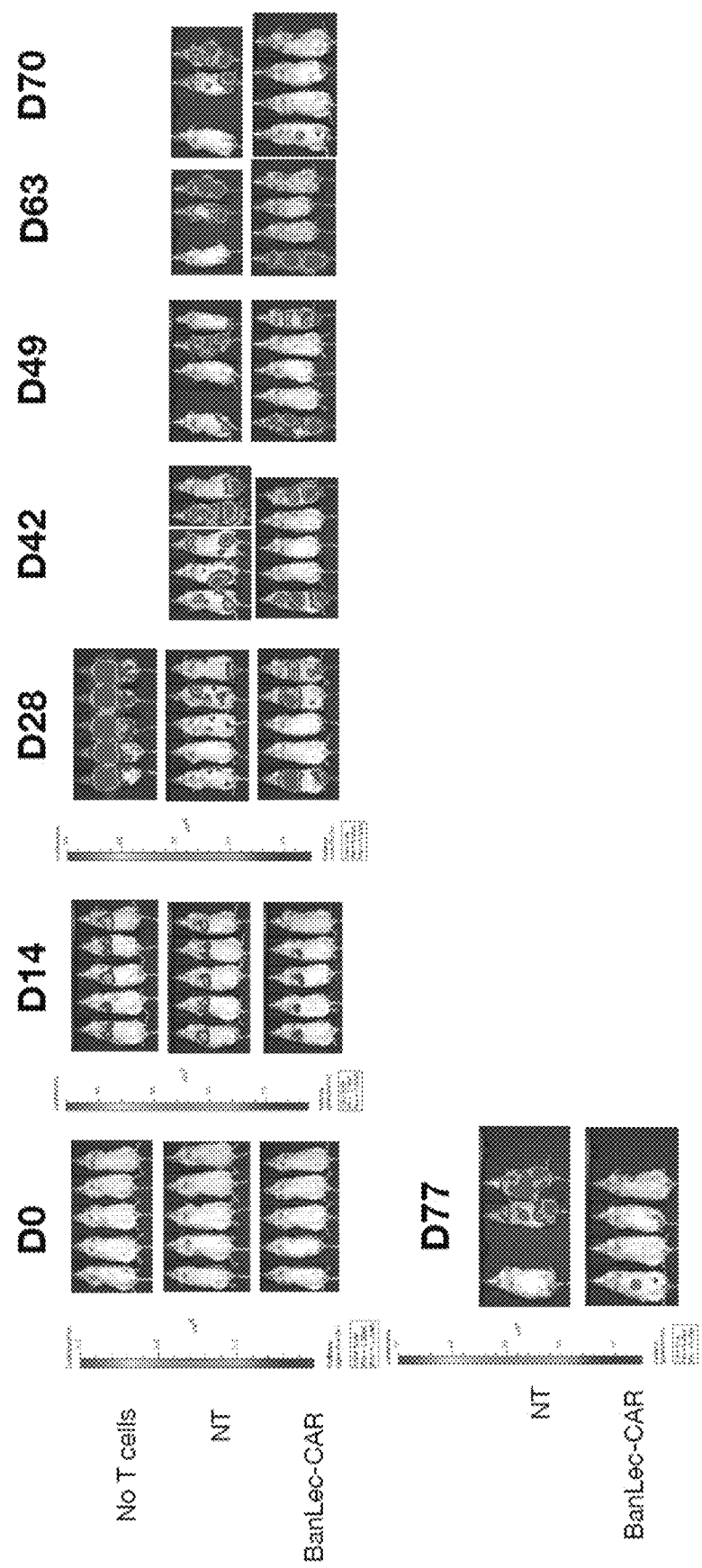
FIG. 4D is a series of representative bioluminenscent images of treated mice to monitor disease progression at D0, D14, D28, D42, D49, D63, D70, and D77 of treatment.

A cytotoxicity assay was performed using the A549 lung cancer cell line cultured with H84T BanLec-CART cells. The leukemia cell line MV411 was used as a control. T cells were plated with a firefly luciferase-expressing A549 lung cancer cell line at specific effector to target ratios. After 18 hours of culture, D-Luciferin was added and bioluminescence was then measured as an indicator of remaining viable A549 cells. Cytotoxicity was then calculated using the formula 100*(experimental release−spontaneous release)/(maximum release−spontaneous release). H84T BanLec-CART cells have specific activity against A549 cells, as shown in FIGS. 3A and 3B.

Standard immunological assays also will be performed with A549 and H1975 lung cancer cell lines using unmodified and BanLec-CART cells as effectors, including co-culture assays, phosphoprotein analysis, ELISA assays, Multiplex cytokine analysis, and cytotoxicity assays. BanLec-CART cells will be evaluated for fratricide, T cell exhaustion, and tonic signaling. BanLec-CART cells are expected to exhibit activation and specific anti-tumor toxicity when exposed to lung tumor cell lines. If suboptimal tumor killing is observed, an unmutated banana lectin (Swanson et al., supra) which is reported to possess T cell activating properties will be incorporated into the CAR. If tumor killing is observed with the unmutated banana lectin CAR, then potential toxicity will be balanced against efficacy in choice of CAR-ectodomain and intracellular signaling components.

Example 3

This example describes experiments for in vivo analysis of BanLec-CART cells.

A xenograft model of human lung cancer was developed. Specifically, mice received $2.5 \times 10^6$ A549.ffLuc cells via tail vein on day 0 (D0). On day 7 (D7) mice received $10^6$ unmodified (NT) T cells, H84T BanLec-CART cells, or no T cells via tail vein (n=5 per group). Disease progression and mouse body weights were monitored by bioluminescence measurement following IP injection of D-Luciferin. H84T BanLec-CART cells have specific activity in A549 cells in vivo, as shown in FIGS. 4A, 4B, 4C, and 4D.

Example 4

This example demonstrates that BanLec CAR-T cells exhibit specific cytotoxicity against lung cancer cells but not normal lung cells.

Figure 5:
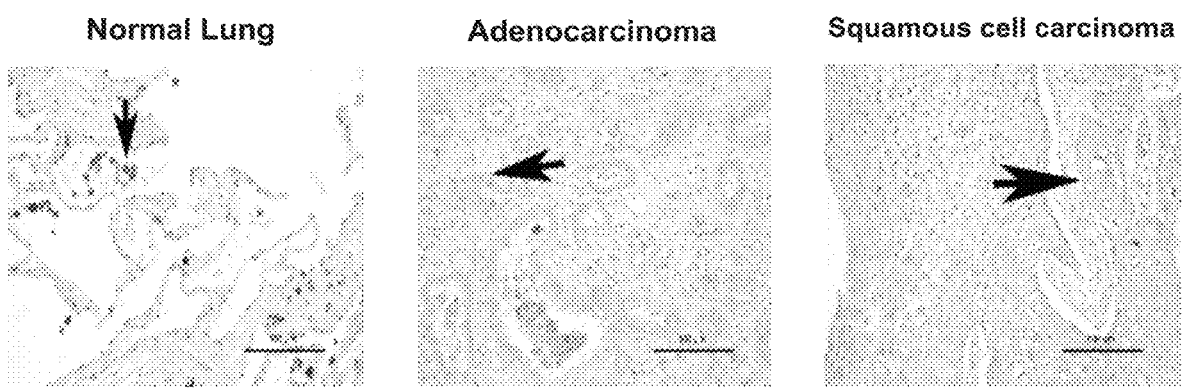
FIG. 5 includes images of immunohistochemistry staining using biotinylated H84T BanLec to probe healthy and NSCLC tissues. Normal lung stains only in macrophages (arrow), which are known to have high mannose on their surface. Adenocarcinoma and squamous cell carcinoma tumors are recognized by H84T in the tumor tissue, as highlighted by the arrows.

Normal and cancerous lung tissues were stained with a "guide compound" comprised of H84T BanLec. As shown in FIG. 5, H84T BanLec bound specifically to tumor cells in two types of non-small cell lung cancer tissue: adenocarcinoma and squamous cell. In normal lung tissue, only macrophages were recognized, as they are known to express high levels of mannose, which is the target of H84T BanLec.

Figure 6A:
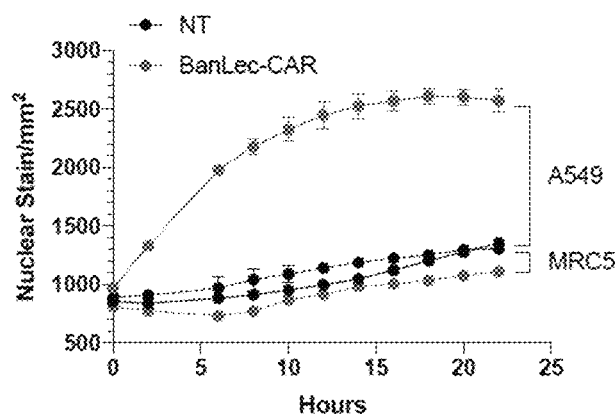
FIG. 6A is a graph illustrating cytotoxicity of BanLec-CAR T cells in A549 and MRC cells. Unmodified T cells (NT) served as a control.
Figure 6B:
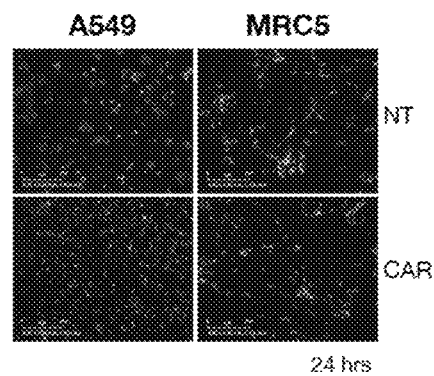
FIG. 6B includes fluorescent images of each treatment condition. Four images were taken per well at each timepoint and three wells were included per condition.

Unmodified (NT) and BanLec-CAR T cells were plated with A549 lung cancer cells or normal lung fibroblasts (MRC5 cell line) at an effector to target ratio of 1:1. Cytotoxicity was measured using a fluorescent reagent that binds nucleic acid. An INCUCYTE™ instrument was used to measure fluorescence over time. Disruption of the cell membrane, as occurs when cells are dying, results in increased staining. BanLec CAR-T cells demonstrated specific cytotoxicity against A459 cells, but were not toxic to MRC5 cells, as shown in FIGS. 6A and 6B.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) polypeptide which comprises a single antigen binding domain comprising a banana lectin extracellular domain, a CD8α transmembrane domain, a 4-1BB co-stimulatory signaling domain, and a CD3 zeta intracellular signaling domain, wherein the banana lectin comprises a substitution of a histidine (H) residue with at threonine (T) residue at amino acid position 84 of a wild type banana lectin comprising the amino acid sequence of SEQ ID NO: 1.

2. The CAR polypeptide of claim 1 further comprising a hinge domain located between the antigen-binding domain and transmembrane domain.

3. The CAR polypeptide of claim 1, further comprising one or more linker segments located between each domain.

4. An engineered lymphocyte expressing the CAR polypeptide of claim 1.

5. The engineered lymphocyte of claim 4, which is a T cell.

6. The engineered lymphocyte of claim 4, which is a natural killer (NK) cell.

7. A nucleic acid molecule comprising a nucleic acid sequence encoding the CAR polypeptide of claim 1.

8. A vector comprising the nucleic acid molecule of claim 7.

9. An engineered lymphocyte comprising the vector of claim 8.

10. The engineered lymphocyte of claim 9, which is a T cell.

11. The engineered lymphocyte of claim 9, which is a natural killer (NK) cell.

12. A method of treating cancer in a subject comprising administering the engineered lymphocyte of claim 4 to the subject.

13. The method of claim 12, wherein the cancer is lung cancer.

* * * * *

UNITED STATES PATENT AND TRADEMARK OFFICE
CERTIFICATE OF CORRECTION

PATENT NO. : 11,760,786 B2  
APPLICATION NO. : 16/782417  
DATED : September 19, 2023  
INVENTOR(S) : Bonifant et al.

Page 1 of 1

It is certified that error appears in the above-identified patent and that said Letters Patent is hereby corrected as shown below:

On the Title Page

Item (72) The Inventorship currently reads:  
Challice L. Bonifant, Towson, MD; (US)  
Alnawaz Rehemtulla, Plymouth, MI; (US)  
David M. Markovitz, Ann Arbor, MI; (US)

It should read:  
Challice L. Bonifant, Towson, MD; (US)  
David M. Markovitz, Ann Arbor, MI; (US)

Signed and Sealed this  
Twenty-ninth Day of July, 2025

Coke Morgan Stewart  
*Acting Director of the United States Patent and Trademark Office*

SEQUENCE LISTING

```
<160> NUMBER OF SEQ ID NOS: 3

<210> SEQ ID NO 1
<211> LENGTH: 143
<212> TYPE: PRT
<213> ORGANISM: Musa acuminata

<400> SEQUENCE: 1

Met Asn Gly Ala Ile Lys Val Gly Ala Trp Gly Gly Asn Gly Gly Ser
1               5                   10                  15

Ala Phe Asp Met Gly Pro Ala Tyr Arg Ile Ile Ser Val Lys Ile Phe
                20                  25                  30

Ser Gly Asp Val Val Asp Gly Val Asp Val Thr Phe Thr Tyr Tyr Gly
            35                  40                  45

Lys Thr Glu Thr Arg His Tyr Gly Gly Ser Gly Gly Thr Pro His Glu
    50                  55                  60

Ile Val Leu Gln Glu Gly Glu Tyr Leu Val Gly Met Ala Gly Glu Val
65                  70                  75                  80

Ala Asn Tyr His Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
                100                 105                 110

Ser Leu Pro Ile Ala Ala Gly Lys Ile Ser Gly Phe Phe Gly Arg Gly
            115                 120                 125

Gly Lys Phe Leu Asp Ala Ile Gly Val Tyr Leu Glu Pro Leu Glu
        130                 135                 140

<210> SEQ ID NO 2
<211> LENGTH: 143
<212> TYPE: PRT
<213> ORGANISM: Artificial Sequence
<220> FEATURE:
<223> OTHER INFORMATION: Synthetic

<400> SEQUENCE: 2

Met Asn Gly Ala Ile Lys Val Gly Ala Trp Gly Gly Asn Gly Gly Ser
1               5                   10                  15

Ala Phe Asp Met Gly Pro Ala Tyr Arg Ile Ile Ser Val Lys Ile Phe
                20                  25                  30

Ser Gly Asp Val Val Asp Gly Val Asp Val Thr Phe Thr Tyr Tyr Gly
            35                  40                  45

Lys Thr Glu Thr Arg His Tyr Gly Gly Ser Gly Gly Thr Pro His Glu
    50                  55                  60
```

-continued

```
Ile Val Leu Gln Glu Gly Glu Tyr Leu Val Gly Met Ala Gly Glu Val
65                  70                  75                  80

Ala Asn Tyr Thr Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
            100                 105                 110

Ser Leu Pro Ile Ala Ala Gly Lys Ile Ser Gly Phe Phe Gly Arg Gly
        115                 120                 125

Gly Lys Phe Leu Asp Ala Ile Gly Val Tyr Leu Glu Pro Leu Glu
    130                 135                 140

<210> SEQ ID NO 3
<211> LENGTH: 432
<212> TYPE: DNA
<213> ORGANISM: Artificial Sequence
<220> FEATURE:
<223> OTHER INFORMATION: Synthetic

<400> SEQUENCE: 3
atgaatggtg cgatcaaagt tggcgcgtgg ggtggcaacg gtggtagcgc ctttgatatg     60
ggcccggcgt atcgtattat tagcgtgaaa atttttagcg gtgatgtggt tgatggcgtt    120
gatgtgacct ttacctatta tggtaaaacc gaaacccgtc attatggcgg tagcggtggt    180
accccgcatg aaattgtgct gcaggaaggt gaatatctgg tgggtatggc gggcgaagtg    240
gcgaactata ctggtgcggt ggtgctgggt aaactgggtt ttagcaccaa taaaaaagcg    300
tatggtccgt ttggcaatac cggcggtacc ccgtttagcc tgccgattgc cgcgggtaaa    360
attagcggct tctttggtcg tggcggtaaa tttctggatg ccattggcgt gtatctggaa    420
ccgctcgagt ga                                                        432
```